United States Patent
Benedetti

(10) Patent No.: US 10,575,982 B2
(45) Date of Patent: Mar. 3, 2020

(54) VASODILATION ASSEMBLY

(71) Applicant: BENEDETTI INTERNATIONAL LIMITED, Wishaw (GB)

(72) Inventor: Giovanni Benedetti, West Kilbride (GB)

(73) Assignee: BENEDETTI INTERNATIONAL LIMITED, Wishaw (GB)

( * ) Notice: Subject to any disclaimer, the term of this patent is extended or adjusted under 35 U.S.C. 154(b) by 419 days.

(21) Appl. No.: 14/442,454

(22) PCT Filed: Nov. 14, 2013

(86) PCT No.: PCT/GB2013/053003
§ 371 (c)(1),
(2) Date: May 13, 2015

(87) PCT Pub. No.: WO2014/076479
PCT Pub. Date: May 22, 2014

(65) Prior Publication Data
US 2016/0058611 A1 Mar. 3, 2016

(30) Foreign Application Priority Data

Nov. 14, 2013 (GB) .................................. 1220450.9

(51) Int. Cl.
*A61F 7/02* (2006.01)
*A61F 7/00* (2006.01)

(52) U.S. Cl.
CPC .......... *A61F 7/02* (2013.01); *A61F 2007/006* (2013.01); *A61F 2007/0029* (2013.01);
(Continued)

(58) Field of Classification Search
CPC ...... A61F 2007/0029; A61F 2007/0059; A61F 7/02; A61F 2007/0233
See application file for complete search history.

(56) References Cited

U.S. PATENT DOCUMENTS 2,706,988 A * 4/1955 Weber .................. A61F 7/0085
34/202
4,452,247 A * 6/1984 Hebert .................. A61D 11/00
607/107

(Continued)

FOREIGN PATENT DOCUMENTS

| CN | 1756522 A | 4/2006 |
| CN | 201304025 Y | 9/2009 |

(Continued)

OTHER PUBLICATIONS

Cornelissen, P., "International Search Report," prepared for PCT/GB2013/053003, dated Mar. 28, 2014, four pages.

*Primary Examiner* — Kaitlyn E Smith
*Assistant Examiner* — Yasamin Ekrami
(74) *Attorney, Agent, or Firm* — Winstead PC

(57) ABSTRACT

The invention relates to a vasodilation assembly for facilitating intravenous cannulation. The assembly comprises: (i) a flexible plastics sleeve (10); (ii) a heated air supply; and (iii) a conduit for conveying heated air from the air supply into the flexible plastics sleeve. The sleeve comprises an air inlet opening (12) for coupling to the conduit, and an opening (14) for accepting an appendage of a patient. The flexible plastics sleeve (10) is of a double-walled construction comprising transparent inner and outer sleeve layers (16, 18).

19 Claims, 6 Drawing Sheets

(52) U.S. Cl.
CPC ............... *A61F 2007/0034* (2013.01); *A61F 2007/0035* (2013.01); *A61F 2007/0036* (2013.01); *A61F 2007/0037* (2013.01); *A61F 2007/0038* (2013.01); *A61F 2007/0039* (2013.01); *A61F 2007/0043* (2013.01); *A61F 2007/0044* (2013.01); *A61F 2007/0045* (2013.01); *A61F 2007/0046* (2013.01); *A61F 2007/0051* (2013.01); *A61F 2007/0059* (2013.01); *A61F 2007/0091* (2013.01); *A61F 2007/0092* (2013.01); *A61F 2007/0244* (2013.01)

(56) References Cited

U.S. PATENT DOCUMENTS

| | | |
|---|---|---|
| 5,044,364 A | 9/1991 | Crowther |
| 5,938,693 A | 8/1999 | Carminucci |
| 6,565,593 B2 | 5/2003 | Diana |
| 6,820,622 B1 * | 11/2004 | Teves ............... A61F 7/0097 128/849 |
| 2004/0243026 A1 | 12/2004 | Toepfer et al. |
| 2006/0026743 A1 | 2/2006 | Farnworth et al. |
| 2006/0271134 A1 * | 11/2006 | Frey ............... A61F 7/02 607/104 |
| 2007/0162096 A1 | 7/2007 | Zakuto et al. |
| 2008/0228245 A1 * | 9/2008 | Schock ............... A61F 7/00 607/104 |
| 2009/0177184 A1 * | 7/2009 | Christensen ......... A61H 9/0057 604/506 |
| 2011/0077723 A1 * | 3/2011 | Parish ............... A61F 5/34 607/104 |

FOREIGN PATENT DOCUMENTS

| | | |
|---|---|---|
| FR | 2544202 A1 | 10/1984 |
| WO | WO-1996028120 A1 | 9/1996 |
| WO | WO-2008070853 A2 | 6/2008 |
| WO | WO-2011085268 A2 | 7/2011 |
| WO | WO-2012012683 A1 | 1/2012 |

* cited by examiner

VASODILATION ASSEMBLY

The present invention relates to a vasodilation assembly and particularly, though not exclusively, to apparatus for facilitating intravenous access to a peripheral vein via cannulation by circulating heated air around a limb in a controlled manner.

BACKGROUND

Intravenous cannulation is a commonly performed invasive medical procedure involving the insertion of a cannula into a vein. Venous access facilitates blood sampling and the administration of fluids, medicines, nutritional supplements, contrast agents for imaging, chemotherapy drugs etc. In some patients difficulties can occur when attempting to locate a suitably prominent vein for venous access. In particular, patients who are young, elderly, obese, of black or Asian ethnicity, or who are intravenous drug users or undergoing regular cannulation—such as during chemotherapy or dialysis courses—may have less prominent peripheral veins. At best, cannulation difficulties can cause embarrassment or inconvenience to the clinician. At worst, it can cause genuine distress to the patient or delay urgent treatment.

Various attempts have been made to overcome the problem of locating a suitable site for venous access. The most common solutions involve gently rubbing or tapping a proposed insertion site, lowering the relevant limb to promote venous engorgement, or applying proximal tourniquets. However, these basic approaches often fail to sufficiently increase vein prominence.

It has also been proposed to apply warm moist towels around the intended cannulation site or to immerse the relevant limb in warm water. More advanced proposals have involved the wearing of electrically heated mitts or gloves by the patient prior to cannulation. Finally, it is also known to apply glyceryl trinitrate (GTN) ointment to the skin prior to attempted cannulation. However, these approaches each have shortcomings or disadvantages. For example, the application of warm moist towels or immersion of a limb in warm water each require a supply of water within a particular temperature range and a plentiful supply of replacement towels for each patient for infection control purposes. Moist towels and water tend to cool rapidly with time and so a consistent and continuous heating effect is not achieved. Commercially available mitts or gloves can be expensive and require strict infection control measures. GTN ointment cannot be applied to a whole limb and so repeated application may be required before a suitable site for venous access is located.

Given that intravenous cannulation is such a common medical procedure, even a modest reduction in the time taken to insert a cannula is important. Accordingly, a requirement exists for apparatus which overcomes or alleviates the shortcomings of prior approaches by providing a consistent, comfortable, safe and convenient means of facilitating intravenous access employing apparatus which is economic to produce as a single use item.

According to a first aspect of the present invention, there is provided a vasodilation assembly for facilitating intravenous cannulation, the assembly comprising:
  (i) a flexible plastics sleeve;
  (ii) a heated air supply; and
  (iii) a conduit for conveying heated air from the air supply into the flexible plastics sleeve;
wherein the sleeve comprises an air inlet opening for coupling to the conduit, and an opening for accepting an appendage of a patient; and wherein the flexible plastics sleeve is of a double-walled construction comprising transparent inner and outer sleeve layers.

By using transparent flexible plastics layers the weight of the sleeve is kept to a minimum whilst allowing both the patient and clinician to view the skin surface of the appendage.

Optionally, the air inlet opening is provided in the outer sleeve layer.

In one embodiment, the air inlet opening is dimensioned so as to be a friction fit over the conduit or any associated end fitting such that no separate fastening means is required.

Optionally, the inner and outer sleeve layers are joined at the proximal end of the flexible plastics sleeve.

The opening at the proximal end of the flexible plastics sleeve therefore allows an appendage of a patient to be placed within the inner sleeve layer.

Optionally, the inner and outer sleeve layers are contiguous and separated by a fold line at the proximal end of the flexible plastics sleeve.

In one embodiment, the flexible plastics sleeve may be manufactured from folded and heat-sealed linear low-density polyethylene (LLDPE) Lay Flat Tubing (LFT). It will be appreciated that alternative materials may be employed such as high-density polyethylene (HDPE), very low-density polyethylene (VLDPE) and low-density polyethylene (LDPE). This list is not exhaustive.

Optionally, an air exit opening is provided in the outer sleeve layer proximate the proximal end of the flexible plastics sleeve.

The positioning of the air exit opening in the outer sleeve layer ensures that heated air is vented away from the patient's body. In practice, for manufacturing simplicity it may be necessary to form openings by making a single incision through both the inner and outer sleeve layers. However, during use, air pressure differentials at each surface of the inner sleeve layer causes it to collapse against the patient's skin ensuring that substantially no heated air passes through the innermost opening. The openings formed in the inner and outer sleeve layers therefore operate in the manner of a valve whereby the innermost opening is maintained in a closed position whilst the outermost opening expands.

Optionally, the inner sleeve layer is closed at its distal end so as to isolate an appendage located therein from incident heated air conveyed through the air inlet into the outer sleeve layer.

Optionally, the most distal extent of the inner sleeve layer is spaced from the air inlet opening at a distal end of the outer sleeve layer so as to maintain a minimum spacing between an appendage located therein and incident heated air conveyed through the air inlet.

Incident air is at its hottest as it enters the air inlet opening and so by maintaining a minimum spacing between it and the most distal extent of the inner sleeve patient discomfort can be minimised or avoided.

Optionally, at least one annular space is provided between the inner and outer sleeve layers and defines an annular passage for the flow of heated air between the air inlet and air exit openings.

Depending upon the specific construction of the flexible plastics sleeve layers there may be a single annular space or two or more annular segments. In one embodiment, where the inner and outer sleeve layers are heat sealed together along their longitudinal edges there is formed two separate annular segments.

Optionally, a nozzle is provided on the conduit for controlling the distribution of heated air from the air supply as it is introduced into the flexible plastics sleeve.

Optionally, the nozzle comprises a projecting surface positioned at its end most distal to the conduit.

In one embodiment, the projecting surface bridges the spacing between the most distal extent of the inner sleeve layer and the air inlet opening. The projecting surface provides a consistent reference point for the placement and support of part of a patient's appendage. For example, a patient's fingers may be rested on the projecting surface.

Optionally, one or more openings are formed in the nozzle at a proximal position relative to its projecting surface.

In one embodiment, openings are distributed circumferentially around the nozzle above and below its projecting surface so as to facilitate an even distribution of warm air annularly around a patient's appendage.

Optionally, a baffle member protrudes out of the surface of the nozzle between the projecting surface and its one or more openings.

The presence of the baffle member deflects the flow of heated air emitted from the opening(s) situated above the nozzle's projecting surface so as to protect the extremities—e.g. fingers—of a patient's appendage.

According to a second aspect of the present invention, there is provided a flexible plastics sleeve for use as part of the vasodilation assembly of the first aspect, the sleeve comprising:
(i) a transparent inner sleeve layer;
(ii) a transparent outer sleeve layer;
(iii) an air inlet opening formed in the outer sleeve layer for coupling to a heated air supply;
(iv) an appendage opening for accepting an appendage of a patient within a compartment defined by the inner sleeve layer;
(v) an air exit opening formed in the outer sleeve layer; and
(vi) at least one annular space provided between the inner and outer sleeve layers defining an annular passage for the flow of heated air between the air inlet and air exit openings.

Optionally, the flexible plastics sleeve is rectangular in shape and sealed along longitudinal edges thereof so as to fasten the inner and outer sleeve layers together and define two annular spaces between the two.

Optionally, the inner and outer sleeve layers are formed from a single piece of linear low-density polyethylene (LLDPE) Lay Flat Tubing (LFT).

Optionally, the inner and outer sleeve layers are contiguous and separated by a fold line proximate the appendage opening of the flexible plastics sleeve.

Optionally, distal edges of the inner sleeve layer lying furthest from the appendage opening are sealed together to provide an enclosed inner compartment.

Optionally, the air inlet opening is formed in the outer sleeve layer at a distal end thereof and is smaller than the appendage opening formed at the opposite proximal end.

Optionally, a linear or non-linear tapered region is formed proximate the air inlet opening by sealing together opposite surfaces of the outer sleeve layer along two lines between each of its longitudinal edges and its lateral edge.

Optionally, a portion of the outer sleeve layer at the air inlet opening extends beyond the remainder of the outer sleeve layer so as to provide a graspable tab facilitating the coupling of the air inlet opening to a heated air supply.

Embodiments of the present invention will now be described, by way of example only, with reference to the accompanying drawings, in which.

Figure 1A:
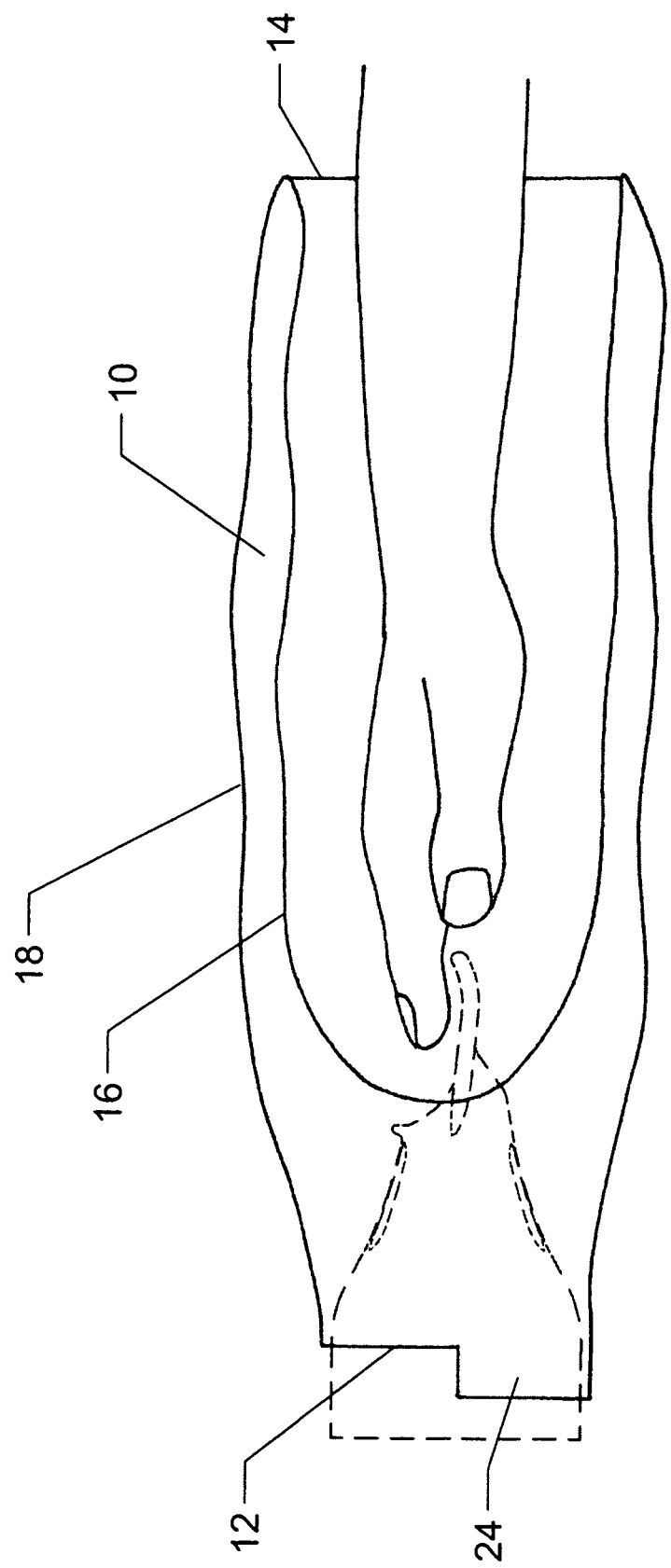
FIG. 1a is a schematic cross-sectional view of a flexible double-walled plastics sleeve forming part of a vasodilation assembly before heated air is introduced therein.

FIG. 1a shows the hand and forearm of a patient placed within an elongate flexible plastics sleeve 10. The sleeve comprises an air inlet opening 12 at a distal end thereof for coupling to the output of a heated air supply (not shown). An appendage opening 14 is provided at the opposing proximal end of the sleeve 10. The appendage opening 14 is larger than the air inlet Opening 12 and dimensioned so as to be capable of receiving hands and forearms of varying sizes and girths. In one example, the dimensions of the sleeve 10 are as follows: length: 56.5 cm; width: 21 cm; width of air inlet opening: 6.5 cm; and width of appendage opening: 20 cm; and it is manufactured from a clear Linear low-density polyethylene (LLDPE) material having a thickness of 30 microns. It will be appreciated that these dimensions are in no way limiting on the scope of the invention and suitable alterations may be made to accommodate different appendages and appendage sizes. Furthermore, the thickness of the polyethylene material may be varied and will usually fall within the range of 12 microns to 100 microns.

Figure 2:
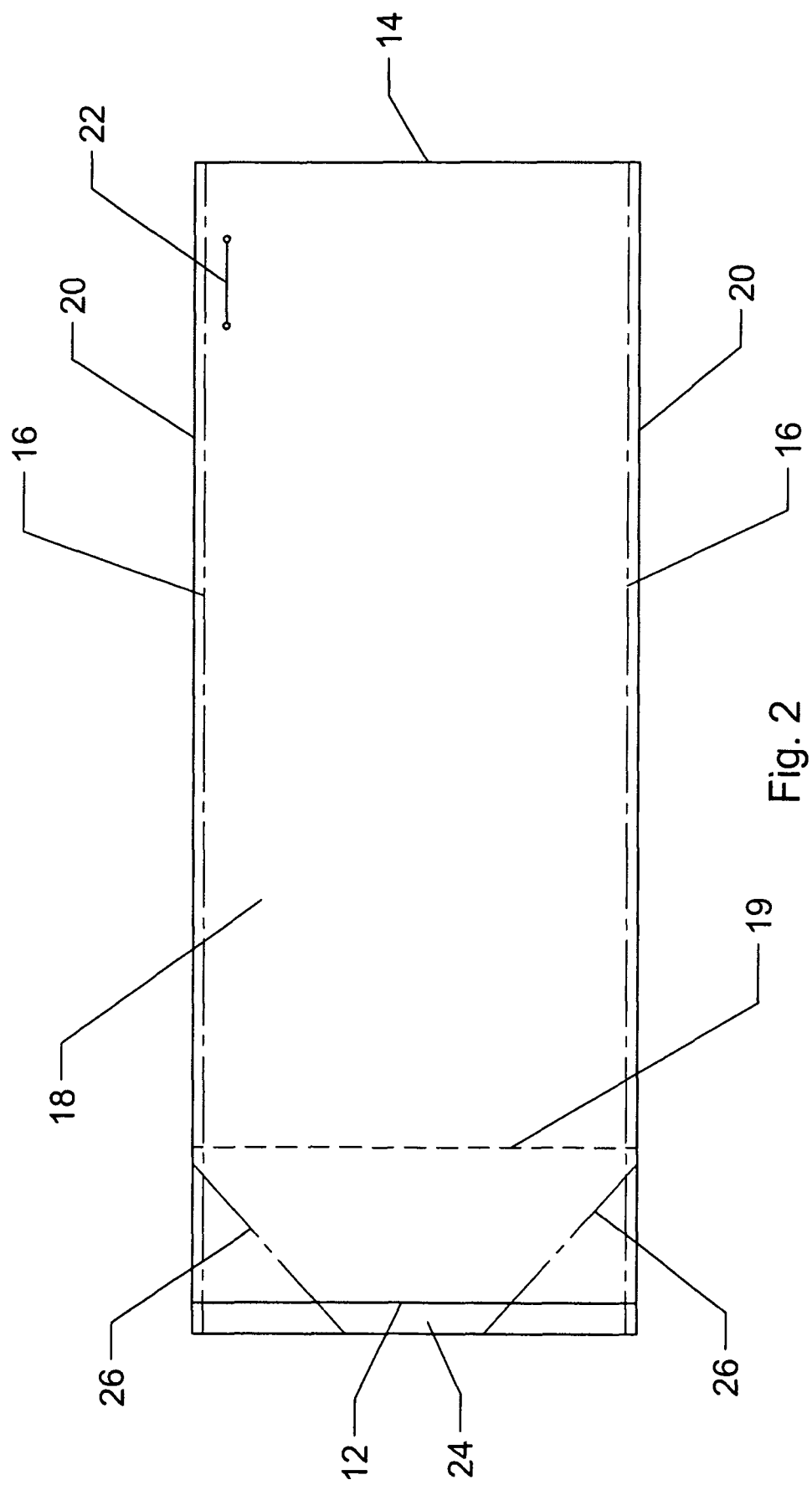
FIG. 2 is a schematic plan view of the flexible plastics sleeve of FIGS. 1a, b.
Figure 3A:
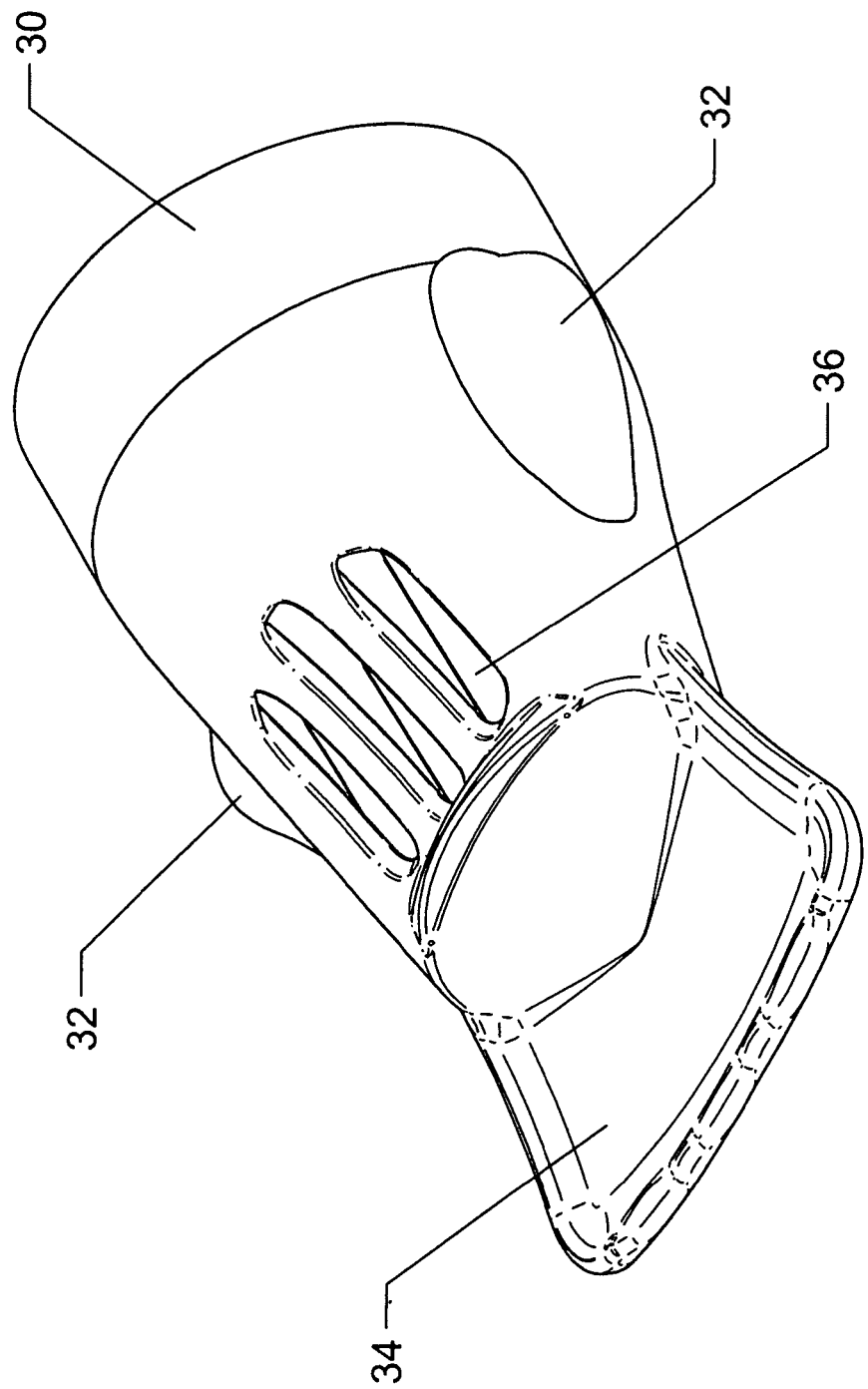
FIGS. 3a-e are perspective side, end, top and bottom views of a nozzle for controlling the distribution of heated air as it is introduced into the flexible plastics sleeve.
Figure 3C:
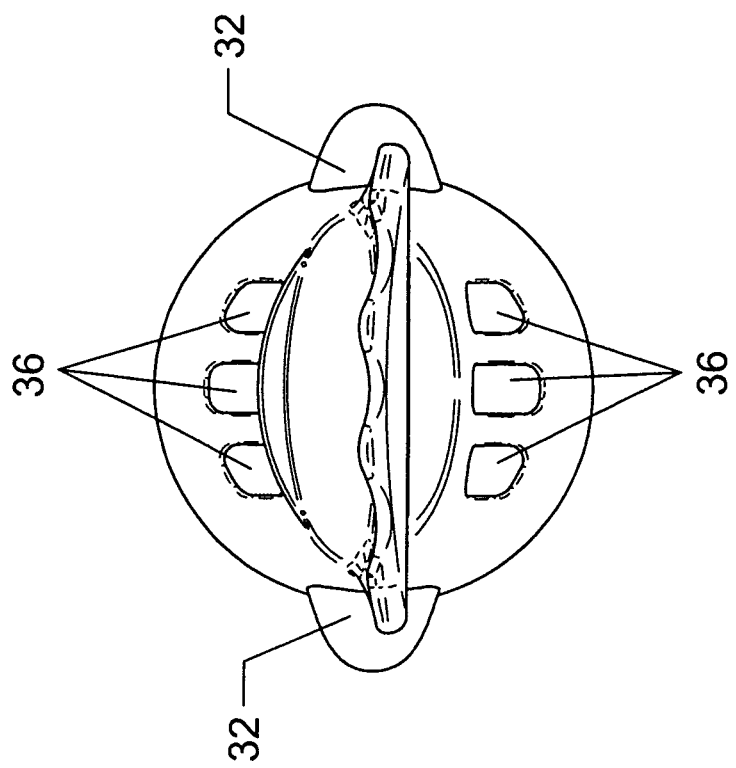
Figure 3B:
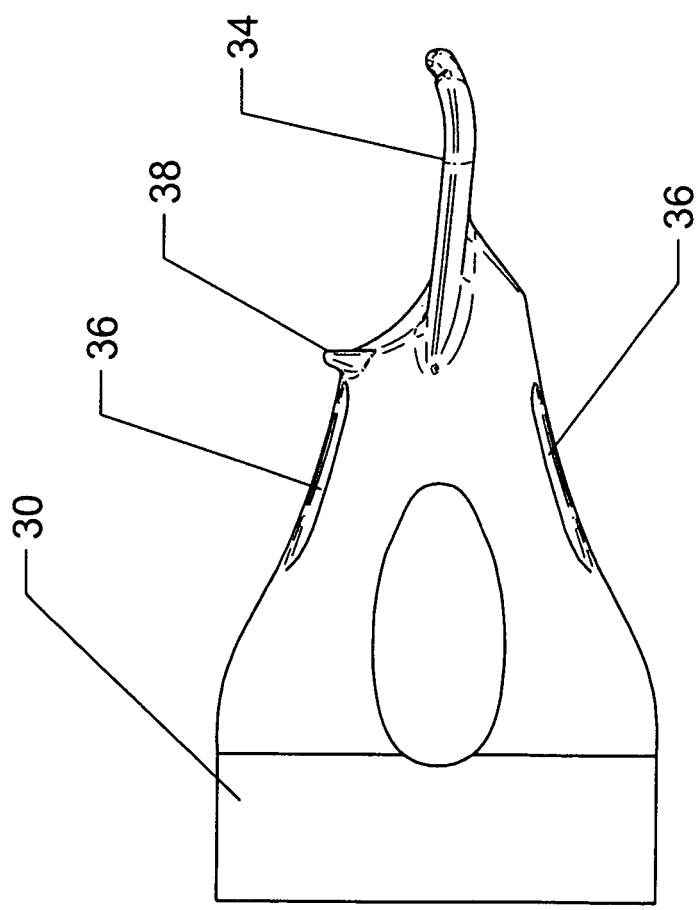
Figure 3E:
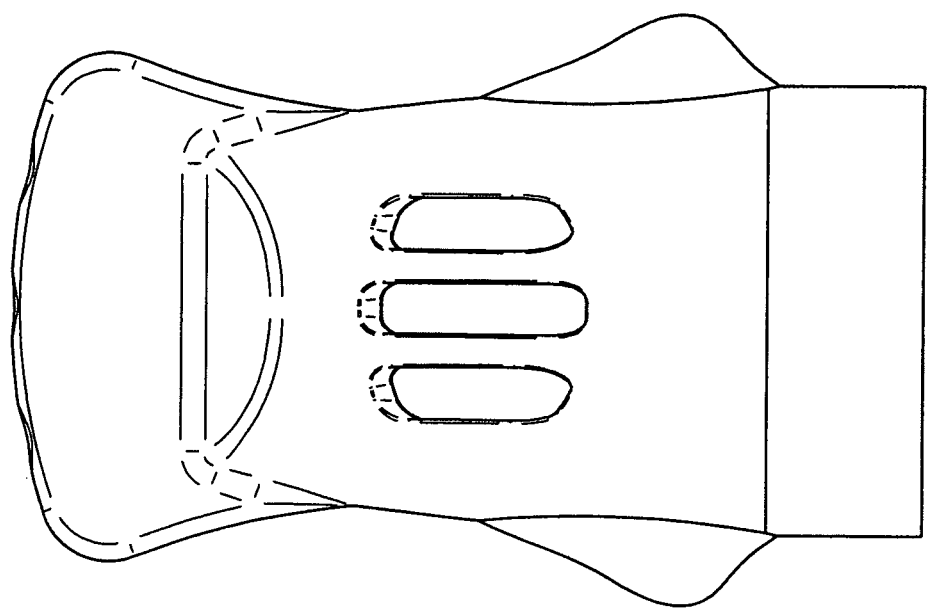
Figure 3D:
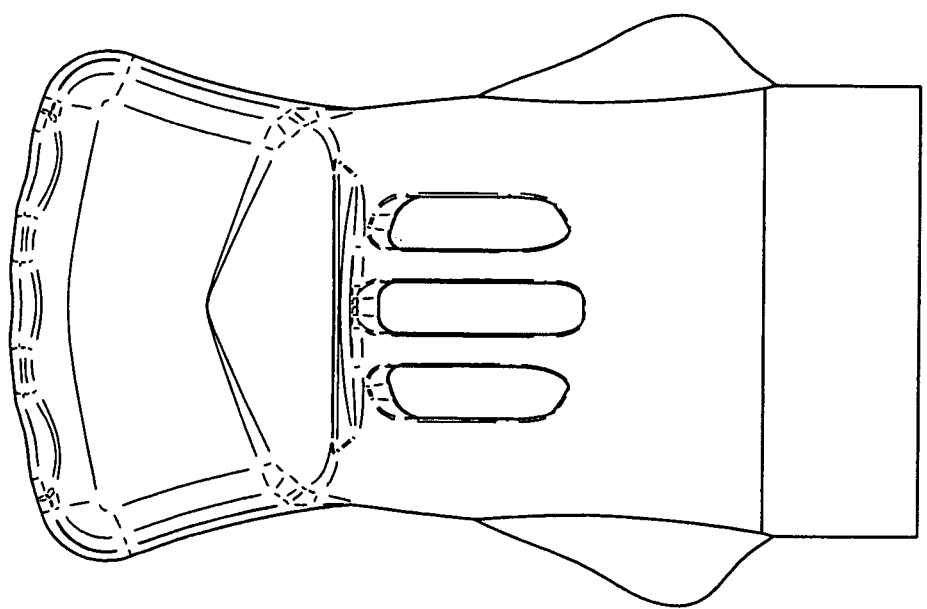

The sleeve 10 is provided with a double-walled construction along the majority of its length. An inner sleeve layer 16 extends within an outer sleeve layer 18 across its full width (see FIG. 2), and from the appendage opening 14 towards the air inlet opening 12. The inner sleeve layer 16 terminates approximately 8 cm from the air inlet opening 12. The inner and outer sleeve layers 16, 18 are heat-sealed together —by means of heat fusion—along their longitudinal edges 20 (see FIG. 2). The most distal edges 19 of the inner sleeve 16 which extend laterally between the opposing longitudinal edges 20 proximate the air inlet opening 12 are likewise heat-sealed together so as to form an isolated double-walled compartment for receipt of a patient's appendage. The most proximal edges of the inner sleeve layer 16 which extend laterally between the opposing longitudinal edges 20 at the appendage opening 14 are contiguous with the outer sleeve layer 18 and the inner and outer sleeve layers 16, 18 are separated by a fold line at the appendage opening 14. In one example, the LLDPE material may conveniently be provided in the form of Lay Flat Tubing (LFT) which simplifies the process of manufacturing the sleeve 10.

The air inlet opening 12 is provided in the outer sleeve layer 18 and is dimensioned so as to be a friction fit over an end fitting (see FIGS. 3a-e). Air exit vents 22 (see FIG. 2)—which may take the form of a incisions or slits through the polyethylene material—are provided proximate the proximal end of the outer sleeve layer 18. Opposing surfaces of the outer sleeve layer 18 are heat-sealed together along lines 26 extending from either side of the air inlet opening 12 to the corresponding longitudinal edge 20. In a non-limiting example, the lines 26 are straight and form approximately 45 degree angles where they meet the longitudinal edges 20 and the distal lateral edge of the outer sleeve layer 18.

In use, the air inlet opening 12 is attached to a nozzle 30 by forcing it past laterally extending lugs 32 serving to retain a friction fit connection between the two. An overhang portion of the outer sleeve layer 18 at the air inlet opening extends beyond the remainder of the outer sleeve layer 18 so as to provide a graspable tab 24 facilitating the manual coupling of the air inlet opening 12 the nozzle 30.

The nozzle 30 comprises a projecting surface 34 at its end most distal to the heated air supply (not shown). The nozzle 30 and its projecting surface 34 bridge the spacing within the outer sleeve layer 18 lying between the most distal extent of the inner sleeve layer 16 and the air inlet opening 12 as shown in dashed lines in FIGS. 1*a*/1*b*. Accordingly, when a patient places their hand and forearm within the isolated compartment defined by the inner sleeve layer 16, the projecting surface 34 provides a reference position onto which three fingers may be placed.

Once the heated air supply is activated, heated air is forced through the openings 36 and is distributed circumferentially around the nozzle above and below its projecting surface 34. In one example, the temperature of the heated air is approximately 59 degrees and a temperature sensor with a safety cut-off is employed to prevent overheating. The openings 36 direct the heated air both upwardly and downwardly with respect to the projecting surface 34 so as to facilitate an even distribution of warm air annularly around a patient's appendage. The presence of a baffle member 38 ensures that heated, air cannot be projected directly onto a patient's fingertips. The heated air is forced into the sleeve 10 by means of a fan and so it fills the two annular segments above and below the inner sleeve layer 16. The heated air vents from the two annular segments via their respective air exit openings 22. The air exit openings are conveniently located on the outer sleeve layer 18 (see FIG. 2) so as to direct vented air away from the patient's body.

Figure 1B:
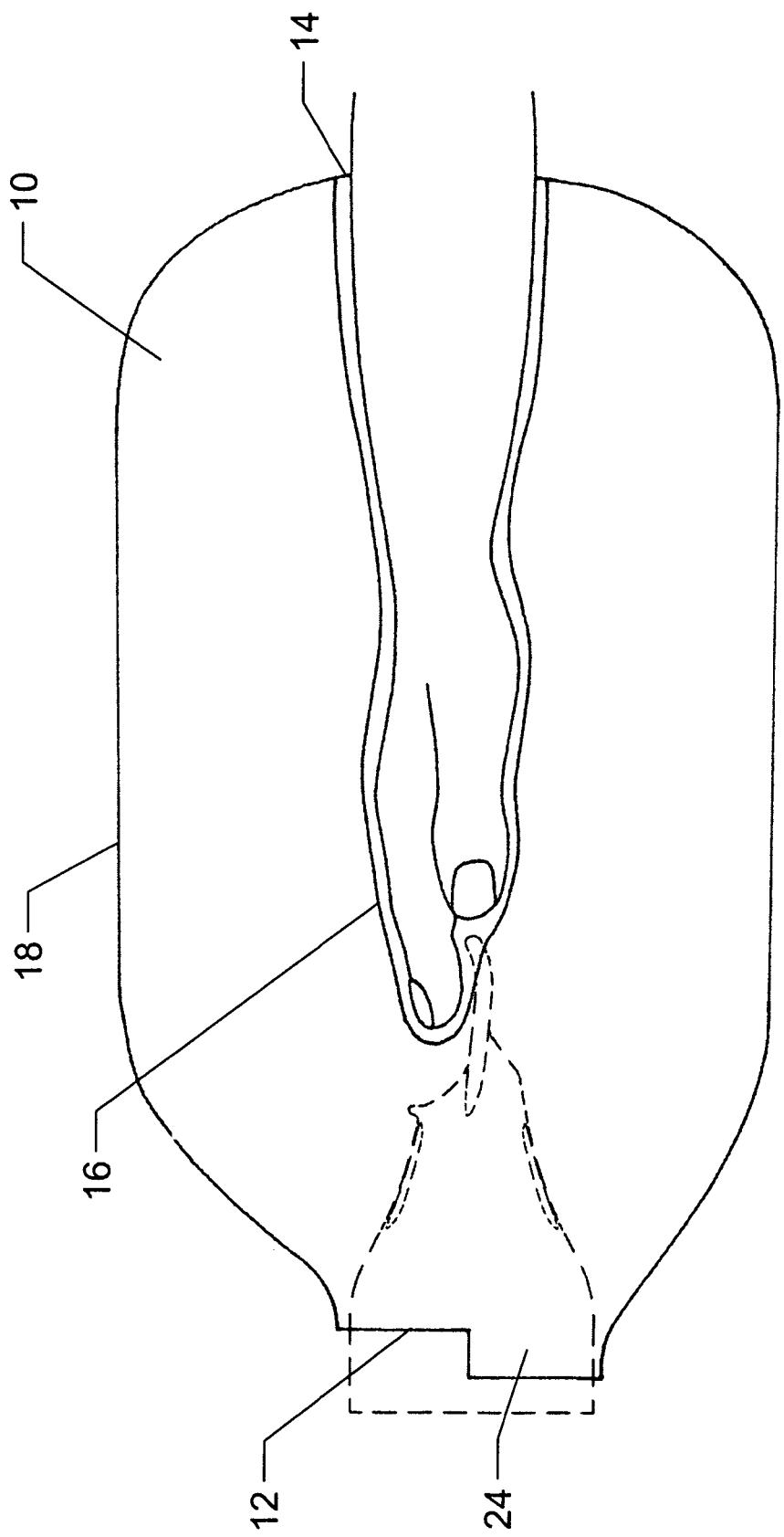
FIG. 1b is a schematic cross-sectional view of the flexible double-walled plastics sleeve as heated air passes through it.

As illustrated in FIG. 1*b* the temperature and pressure differential existing between the compartment defined by the inner sleeve layer 16 and the respective annular segments causes the inner sleeve layer 16 to collapse against the skin of the patient. In doing so, this facilitates efficient heat transfer through the inner sleeve layer 16 onto around the entire exposed skin surface of the patient. Importantly, this occurs without the patient's skin coming into direct contact with any heated air.

It will be appreciated that this apparatus of the present invention provides a means of achieving vasodilation in a consistent and controlled manner which is both convenient for the clinician and comfortable for the patient.

Modifications and improvements may be made to the foregoing without departing from the scope of the invention as defined by the accompanying claims. For example, whilst two sleeve layers are described and illustrated, more than two layers could be employed. Whilst the sleeve has been described and illustrated as receiving a hand and arm of a patient, suitable adaptations could of course be made to accommodate other body parts such as the foot and leg.

Unless the context allows otherwise, the terms distal and proximal are to be understood as describing positions with respect to a patient's body.

The invention claimed is:

1. A vasodilation assembly for facilitating intravenous cannulation, the vasodilation assembly comprising:
   (i) a flexible plastics sleeve;
   (ii) a heated air supply; and
   (iii) a conduit for conveying heated air from the heated air supply into the flexible plastics sleeve;
   wherein the flexible plastics sleeve is of a double-walled construction comprising inner and outer sleeve layers forming an annular space between the inner and outer sleeve layers;
   wherein the flexible plastics sleeve comprises an air inlet opening at a distal end of the flexible plastics sleeve for coupling the annular space to the conduit, and an appendage opening at a proximal end of the flexible plastics sleeve opposite the distal end for accepting an appendage of a patient within a compartment defined by the inner sleeve layer; and
   wherein the annular space defines an annular passage comprising two annular segments for a flow of heated air between the air inlet opening and an air exit opening provided in each annular segment, each air exit opening being provided in the outer sleeve layer proximate the proximal end of the flexible plastics sleeve; and
   wherein the flexible plastics sleeve is sealed along longitudinal edges thereof so as to fasten the inner and outer sleeve layers together and define the two annular segments between the inner sleeve layer and the outer sleeve layer.

2. The vasodilation assembly according to claim 1, wherein the air inlet opening is provided in the outer sleeve layer.

3. The vasodilation assembly according to claim 1, wherein the inner sleeve layer and the outer sleeve layer are joined at the proximal end of the flexible plastics sleeve.

4. The vasodilation assembly according to claim 1, wherein the inner sleeve layer and the outer sleeve layer are contiguous and separated by a fold line at the proximal end of the flexible plastics sleeve.

5. The vasodilation assembly according to claim 1, wherein a most distal extent of the inner sleeve layer is spaced from the air inlet opening at a distal end of the outer sleeve layer so as to maintain a spacing between an appendage located therein and incident heated air conveyed through the air inlet opening.

6. The vasodilation assembly according to claim 1, wherein a nozzle is provided on the conduit for controlling a distribution of heated air from the heated air supply as it is introduced into the flexible plastics sleeve.

7. The vasodilation assembly according to claim 6, wherein the nozzle comprises a projecting surface positioned at its end most distal to the conduit.

8. The vasodilation assembly according to claim 7, wherein one or more openings are formed in the nozzle at a proximal position relative to its projecting surface.

9. The vasodilation assembly according to claim 8, wherein a baffle member protrudes out of a surface of the nozzle between the projecting surface and its one or more openings.

10. The vasodilation assembly according to claim 1, wherein the flexible plastics sleeve is rectangular in shape and sealed along longitudinal edges thereof so as to fasten the inner and outer sleeve layers together and define the two annular segments between the inner sleeve layer and the outer sleeve layer.

11. The vasodilation assembly according to claim 1, wherein the inner and outer sleeve layers are transparent.

12. A flexible plastics sleeve for use as part of the vasodilation assembly of claim 1, the flexible plastics sleeve comprising:
   (i) an inner sleeve layer;
   (ii) an outer sleeve layer;

(iii) an air inlet opening formed in the outer sleeve layer at a distal end of the flexible plastics sleeve for coupling to a heated air supply;

(iv) an appendage opening at a proximal end of the flexible plastics sleeve opposite the distal end for accepting an appendage of a patient within a compartment defined by the inner sleeve layer; and (v) an annular space provided between the inner sleeve layer and the outer sleeve layer defining an annular passage comprising two annular segments for a flow of heated air between the air inlet opening and an air exit opening provided in each annular segment, each air exit opening being provided in the outer sleeve layer proximate the proximal end of the flexible plastics sleeve, wherein the flexible plastics sleeve is sealed along longitudinal edges thereof so as to fasten the inner and outer sleeve layers together and define the two annular segments between the inner sleeve layer and the outer sleeve layer.

13. The flexible plastics sleeve as claimed in claim 12, wherein the flexible plastics sleeve is rectangular in shape.

14. The flexible plastics sleeve as claimed in claim 12, wherein the inner sleeve layer and the outer sleeve layer are formed from a single piece of linear low-density polyethylene (LLDPE) Lay Flat Tubing (LFT).

15. The flexible plastics sleeve as claimed in claim 12, wherein the inner sleeve layer and the outer sleeve layer are contiguous and separated by a fold line proximate the appendage opening of the flexible plastics sleeve.

16. The flexible plastics sleeve as claimed in claim 12, wherein distal edges of the inner sleeve layer lying furthest from the appendage opening are sealed together to provide the compartment defined by the inner sleeve layer.

17. The flexible plastics sleeve as claimed in claim 12, wherein the air inlet opening is formed in the outer sleeve layer at a distal end thereof and is smaller than the appendage opening formed at the opposite proximal end.

18. The flexible plastics sleeve as claimed in claim 13, wherein a linear or non-linear tapered region is formed proximate the air inlet opening by sealing together opposite surfaces of the outer sleeve layer along two lines between each of its longitudinal edges and its lateral edge.

19. The flexible plastics sleeve according to claim 12, wherein the inner and outer sleeve layers are transparent.

\* \* \* \* \*